United States Patent [19]

Skidmore et al.

[11] Patent Number: 4,937,268

[45] Date of Patent: Jun. 26, 1990

[54] CHEMICAL COMPOUNDS

[75] Inventors: Ian F. Skidmore, Welwyn; Harry Finch, Letchworth; Alan Naylor, Royston; Lawrence H. C. Lunts, Broxbourne; David Hartley, Knebworth; William L. Mitchell, London, all of England

[73] Assignee: Glaxo Group Limited, London, England

[21] Appl. No.: 166,975

[22] Filed: Mar. 11, 1988

[30] Foreign Application Priority Data

Mar. 12, 1987 [GB] United Kingdom ............... 8705919
Feb. 29, 1988 [GB] United Kingdom ............... 8804703

[51] Int. Cl.$^5$ .................................... C07C 91/34
[52] U.S. Cl. .................................... 514/651; 564/346; 546/157; 546/158; 546/300
[58] Field of Search .................. 560/108; 564/346; 514/651

[56]     References Cited
    FOREIGN PATENT DOCUMENTS

| 0162576 | 11/1985 | European Pat. Off. | 560/108 |
| 178919 | 4/1986 | European Pat. Off. | 560/108 |
| 2140800 | 12/1984 | United Kingdom | 560/108 |
| 2159151 | 11/1985 | United Kingdom | 560/108 |
| 2162842A | 2/1986 | United Kingdom | 560/108 |
| 2165542A | 4/1986 | United Kingdom | 560/108 |

*Primary Examiner*—Mary C. Lee
*Assistant Examiner*—Zinna Northington-Davis

[57]  ABSTRACT

This invention relates to compounds of the general formula (I)

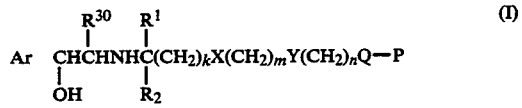

and physiologically acceptable salts and solvates thereof wherein
Ar represents

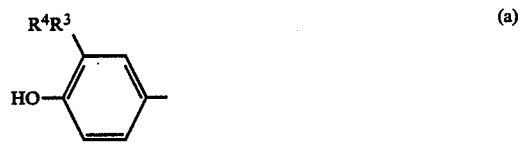

where
$R^3$ is a bond or a straight or branched $C_{1-2}$alkylene group,
$R^4$ is a hydroxy group or a group $R^5NH$— where $R^5$ represents a group $CH_3SO_2$—, HCO— or $NH_2CO$—,

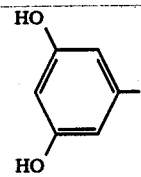

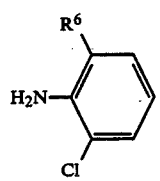

where $R^6$ is a chlorine atom or the group $F_3C$—,

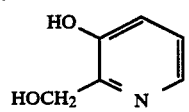

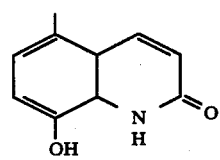

or

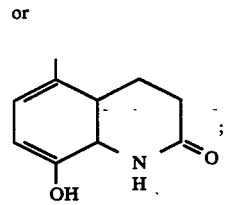

k represents an integer from 1 to 8,
m represents zero or an integer from 2 to 7 and
n represents an integer from 2 to 7 with the proviso that the sum total of k, m and n is 4 to 12;
$R^1$ and $R^2$ each represents a hydrogen atom or a methyl or ethyl group with the proviso that the sum total of carbon atoms in $R^1$ and $R^2$ is not more than 2;
$R^{30}$ represents hydrogen or $C_{1-2}$alkyl;
X represents an oxygen or sulphur atom; and
Y and Q may each represent a bond or an oxygen or sulphur atom with the provisos that at least one of Y and Q represents an oxygen or sulphur atom and when Y is a bond m is zero, or when Y represents an oxygen or sulphur atom m is an integer from 2 to 7;
P represents a phenyl group optionally substituted by one or more substituents selected from halogen atoms, or the groups $C_{1-3}$alkyl, $C_{1-3}$alkoxy, hydroxy, —$CH_2OH$—, —$(CH_2)_2OH$, —$CO_2H$, —$CO_2CH_3$, —$CO_2(CH_2)_2CH_3$, —$R^7$, $COR^7$, —$NHCOR^8$ and —$NR^9SO_2R^{10}$; where
$R^7$ represents an amino, amino$C_{1-3}$alkyl, amino$C_{1-}$ (Abstract continued on next page.)

$_3$dialkyl, pyrrolidino, piperidino, hexamethyleneimino, piperazino, N-methylpiperazino or morpholino group;

$R^8$ represents a hydrogen atom or a $C_{1-4}$alkyl, $C_{1-4}$alkoxy, phenyl or amino group;

$R^9$ represents a hydrogen atom or a methyl group;

$R^{10}$ represents a methyl, phenyl, amino or dimethylamino group;

or P represents a pyridyl group optionally substituted by one or two substitutents selected from halogen atoms or hydroxy, $C_{1-3}$alkyl and $C_{1-3}$alkoxy groups.

The compounds have a stimulant action at $\beta_2$-adrenoreceptors and are useful, in particular, in the treatment of diseases associated with reversible airways obstruction such as asthma and chronic bronchitis.

10 Claims, No Drawings

CHEMICAL COMPOUNDS

This invention relates to novel ethanolamine derivatives having a stimulant action at $\beta_2$-adreno- receptors, to processes for their preparation, to pharmaceutical compositions containing them and to their use in medicine.

Thus the present invention provides compounds of the general formula (I)

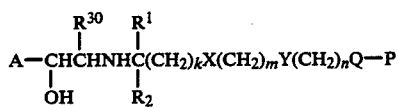
(I)

and physiologically acceptable salts and solvates (e.g. hydrates) thereof wherein Ar represents

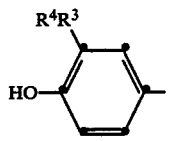
(a)

where
$R^3$ is a bond or a straight or branched $C_{1-2}$ alkylene group,
$R^4$ is a hydroxy group or a group $R^5NH$— where $R^5$ represents a group $CH_3SO_2$—, $HCO$— or $NH_2CO$—,

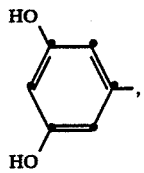
(b)

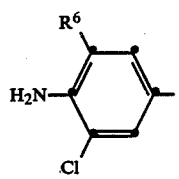
(c)

where $R^6$ is a chlorine atom or the group $F_3C$—,

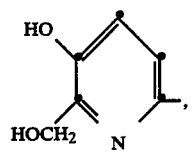
(d)

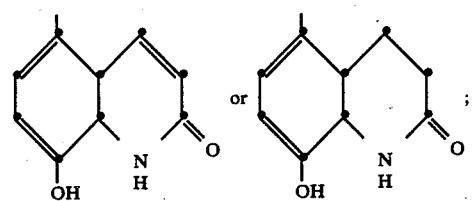
(e)

k represents an integer from 1 to 8,
m represents zero or an integer from 2 to 7 and
n represents an integer from 2 to 7 with the proviso that the sum total of k, m and n is 4 to 12;
$R^1$ and $R^2$ each represents a hydrogen atom or a methyl or ethyl group with the proviso that the sum total of carbon atoms in $R^1$ and $R^2$ is not more than 2;
$R^{30}$ represents hydrogen or $C_{1-2}$ alkyl;
X represents an oxygen or sulphur atom; and
Y and Q may each represent a bond or an oxygen or sulphur atom with the provisos that at least one of Y and Q represents an oxygen or sulphur atom and when Y is a bond m is zero, or when Y represents an oxygen or sulphur atom m is an integer from 2 to 7;
P represents a phenyl group optionally substituted by one or more substituents selected from halogen atoms, or the groups, $C_{1-3}$ alkyl, $C_{1-3}$ alkoxy, hydroxy, —$CH_2OH$, —$(CH_2)_2OH$, —$CO_2H$, —$CO_2CH_3$, —$CO_2(CH_2)_2CH_3$, —$R^7$, $COR^7$, —$NHCOR^8$ or —$NR^9SO_2R^{10}$; where
$R^7$ represents an amino, amino$C_{1-3}$alkyl, amino$C_{1-3}$dialkyl, pyrrolidino, piperidino, hexamethyleneimino, piperazino, N-methylpiperazino or morpholino group;
$R^8$ represents a hydrogen atom or a $C_{1-4}$ alkyl, $C_{1-4}$ alkoxy, phenyl or amino group;
$R^9$ represents a hydrogen atom or a methyl group;
$R^{10}$ represents a methyl, phenyl, amino or dimethylamino group; or P represents a pyridyl group optionally substituted by one or two substituents selected from halogen atoms or hydroxy, $C_{1-3}$ alkyl or $C_{1-3}$ alkoxy groups;

It will be appreciated that the compounds of general formula (I) possess one or more asymmetric carbon atoms, namely the carbon atom of the $$-\underset{\underset{OH}{|}}{CH}-$$

group and, when $R^1$ and $R^2$ are different groups or $R^{30}$ is not hydrogen atom, the carbon atom(s) to which these are attached.

The compounds according to the invention thus include all enantiomers, diastereoisomers and mixtures thereof, including racemates. Compounds in which the carbon atom in the $$-\underset{\underset{OH}{|}}{CH}-$$

group is in the R configuration are preferred.

In the general formula (I), the chain —$(CH_2)_k$— may be for example —$CH_2$—, —$(CH_2)_2$—, —$(CH_2)_3$—, —$(CH_2)_4$—, —$(CH_2)_5$—, —$(CH_2)_6$— or —$(CH_2)_7$—. The chains —$(CH_2)_m$— and —$(CH_2)_n$— may be for example —$(CH_2)_2$—, —$(CH_2)_3$—, —$(CH_2)_4$—, —$(CH_2)_5$— or —$(CH_2)_6$—, or the chain —$(CH_2)_m$— may be a bond.

In general, the total number of carbon atoms in the chains —$(CH_2)_k$—, —$(CH_2)_m$— and —$(CH_2)_n$— is preferably 6 to 12 inclusive and may be for example 7, 8, 9 or 10. Compounds wherein the sum total of carbon atoms in the chains —$(CH_2)k$—, —$(CH_2)_m$— and —$(CH_2)_n$— is 7, 8 or 9 are particularly preferred.

In the compounds of formula (I) R¹ and R², for example, may each be methyl or ethyl groups except that if one of R¹ and R² is an ethyl group, the other is a hydrogen atom. R¹ and R² are each preferably a hydrogen atom or a methyl group.

R³⁰ in the compounds of formula (I) may represent for example a methyl or ethyl group or particularly a hydrogen atom.

In the definition of Ar in compounds of formula (I), R³ may be, for example,

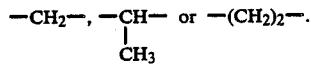

Ar in compounds of formula (I) may be for example

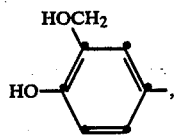 (f)

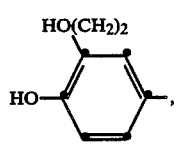 (g)

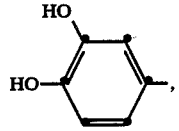 (h)

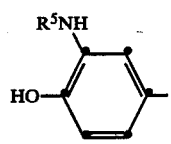 (i)

(where R⁵ is HCO—, NH₂CO—, or CH₃SO₂—),

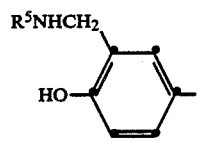 (j)

(where R⁵ is as just defined), or a group of type (b), (c), (d) or (e).

Preferred compounds are those of formula (I) wherein Ar represents a group of type (b), (c), (d), (f), or (i).

Particularly preferred compounds from within this group are compounds of formula (I) wherein Ar represents a group of type (c), (f) or i; (where R⁵ is CH₃SO₂—). Especially preferred are compounds were Ar represents a group of type c; (where R⁶ is a chlorine atom) or a group of type (f).

P may for example represent a phenyl group. Examples of the optional substituents which may be present on the phenyl group represented by P include bromine, iodine, chlorine, fluorine, methyl, ethyl, methoxy, ethoxy, amino, methylamino, ethylamino, dimethylamino diethylamino, morpholino, piperidino, piperazino, N-methylpiperazino, —NHCHO, —NHCOR⁸ [where R⁸ is C₁₋₄ alkyl, (e.g. methyl, ethyl, isopropyl or n-butyl), C₁₋₄ alkoxy (e.g. methoxy, ethoxy, isopropoxy or n-butoxy), phenyl or amino], —NHSO₂CH₃, —NR⁹SO₂R¹⁰, (where R⁹ represents a hydrogen atom or a methyl group and R¹⁰ represents methyl, phenyl, amino or dimethylamino), —COOH, —COOCH₃, —COO(CH₂)₂CH₃, —CON(CH₂CH₃)₂, —CONH₂, —CON(CH₃)₂,

hydroxyl, —CH₂OH, or —(CH₂)₂OH.

The phenyl group represented by P may for example contain one, two or three substituents, which may be present at the 2-, 3-, 4-, 5- or 6-positions on the phenyl ring.

Preferred compounds are those of formula (I) wherein P represents an optionally substituted phenyl group containing one or two substituents selected from halogen (e.g. chlorine) atom(s), C₁₋₆ alkyl (e.g. methyl) or C₁₋₆ alkoxy (e.g. methoxy) groups or the groups —NHCOCH₃, —CO₂(CH₂)₂CH₃ or —CON(CH₂CH₃)₂.

P may also for example represent a pyridyl group. This may be attached to the rest of the molecule at either the 2-, 3-, or 4-position.

When the pyridyl group is substituted, the substituents may be at the 2-, 3-, 4-, 5- or 6-position(s) in the ring. When the pyridyl group is substituted by one or two halogen atoms, these may be fluorine, chlorine or bromine. Preferably, when substituted, the pyridyl group is attached to the rest of the molecule at the 2-position and it contains a single substituent at the 3-, 5- or 6-position.

A preferred group of compounds are those of formula (I) in which P represents an optionally substituted pyridyl group, and more especially a pyridyl group attached to the rest of the molecule at the 2-, 3- or 4-position, and optionally containing a single substituent selected from hydroxy, C₁₋₃ alkyl (e.g. methyl), C₁₋₃ alkoxy (e.g. methoxy) or halogen (e.g. bromine). Within this group particularly preferred compounds are those in which P is an unsubstituted pyridyl group.

In the general formula (I) X may represent an oxygen or sulphur atom and Y and Q may each represent a bond or an oxygen or sulphur atom.

A preferred group of compounds are those of formula (I) in which X is an oxygen atom. Also preferred are compounds of formula (I) where Y represents a bond or an oxygen or sulphur atom. Another group of preferred compounds are those of formula (I) where Q represents a bond or an oxygen or sulphur atom.

Preferred compounds from within this group are those wherein Y is a bond and Q is an oxygen or sulphur atom.

Additional preferred compounds are those of formula (I) where X is an oxygen atom, Y is a sulphur or more preferably an oxygen atom and Q is a bond. Another group of preferred compounds are those of formula (I) wherein X is an oxygen atom, Y is an oxygen atom and Q is an oxygen atom.

Preferred compounds according to the invention are 4-hydroxy-α¹-[[[6-[(4-phenylthio)butoxy]hexyl]amino]methyl]-1,3-benzenedimethanol, 4-[3-[[6-[[2-(4-amino-3,5-dichlorophenyl)-2-hydroxyethyl]amino]hexyl]oxy]propyl]-N,N-diethylbenzamide, 4-hydroxy-α¹-[[[3-[2-(4-phenylbutoxy)ethoxy]propyl]amino]methyl]-1,3-benzenedimethanol, 4-amino-3,5-dichloro-α-[[[3-[2-(3-phenoxypropoxy)ethoxy]propyl]amino]methyl]benzenemethanol, 4-amino-3,5-dichloro-α-[[[3-[2-(3-phenylpropoxy)ethoxy]propyl]amino]methyl]benzenemethanol,

[4-amino-3,5-dichloro-α-[[[6-[2-[[2-(2-pyridinyl)ethyl]thio]ethoxy]hexyl]amino]methyl]benzenemethanol and their physiologically acceptable salts and solvates.

A further preferred compound according to the invention is 4-hydroxy-α¹-[[[3-[2-[3-(4-acetamido)phenylpropoxy]ethoxy]propyl]amino]methyl]-1,3-benzenedimethanol.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, benzenesulphonates, p-toluenesulphonates, naphthalenesulphonates, methanesulphonates, sulphamates, ascorbates, salicylates, acetates, diphenylacetates, triphenylacetates, adipates, fumarates, succinates, lactates, glutarates, gluconates, tricarballylates, hydroxy-naphthalenecarboxylates (e.g. 1-hydroxy- or 3-hydroxy-2-naphthalenecarboxylates including 4,4'-methylenebis(3-hydroxy-2-naphthalenecarboxylic acid), or oleates. The compounds may also form salts with suitable bases. Examples of such salts include alkali metal (e.g. sodium and potassium), and alkaline earth metal (e.g. calcium or magnesium) salts.

The compounds according to the invention have a stimulant action at $\beta_2$-adrenoreceptors, which furthermore is of a particularly advantageous profile. The stimulant action was demonstrated in the isolated trachea of the guinea-pig, where compounds were shown to cause relaxation of contractions induced by PGF ε or electrical stimulation. Compounds according to the invention have shown a particularly desirable duration of action in these tests.

The compounds according to the invention may be used in the treatment of diseases associated with reversible airways obstruction such as asthma and chronic bronchitis.

The compounds according to the invention are also indicated as useful for the treatment of inflammatory and allergic skin diseases, congestive heart failure, depression, premature labour, glaucoma and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in conventional manner.

The compounds of the invention may be formulated for parenteral administration by bolus injection or continuous infusion. Formulations for injection may be presented in unit dosage form in ampoules, or in multi-dose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use. For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

In the following description relating to the preparation of compounds of formula (I) and intermedfates used in the preparation thereof, k, m, n, Ar, $R^1$, $R^2$, $R^{30}$ X, Y, P and Q are as defined for general formula (I) unless otherwise specified. Any hydroxy and/or amino groups present in the starting materials may need to be in a protected form and the final step may be the removal of a protecting group. Suitable protecting groups and methods for their removal are for example those described in "Protective Groups in Organic Chemistry", by Theodora Greene (John Wiley and Sons Inc. 1981). Thus hydroxyl groups may for example be protected by arylmethyl groups such as benzyl, diphenylmethyl or triphenylmethyl, or as tetrahyropyranyl derivatives. Suitable amino protecting groups include arylmethyl groups such as benzyl, α-methylbenzyl, diphenylmethyl or triphenylmethyl, and acyl groups such as acetyl, trichloroacetyl or trifluoroacetyl. Conventional methods of deprotection may be used. Thus for example arylmethyl groups may be removed by hydrogenolysis in the presence of a metal catalyst (e.g. palladium on charcoal). Tetrahydropyranyl groups may be cleaved by hydrolysis under acidic conditions. Acyl groups may be removed by hydrolysis with a base such as sodium hydroxide or potassium carbonate, or a group such as trichloroacetyl may be removed by reduction with, for example, zinc and acetic acid.

The compounds according to the invention may be prepared by a number of processes.

In one general process (1), a compound of general formula (I) may be prepared by alkylation, using conventional alkylation procedures.

Thus, for example in one process (a), a compound of general formula (I) in which $R^1$ is a hydrogen atom may be prepared by alkylation of an amine of general formula (II)

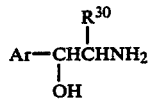
(II)

followed where necessary by removal of any protecting groups.

The alkylation (a) may be effected using an alkylating agent of general formula (III):

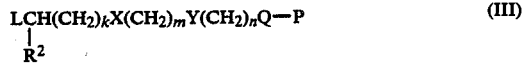
(III)

(wherein L represents a leaving group, for example a halogen atom such as chlorine, bromine or iodine, or a hydrocarbylsulphonyloxy group such as methanesulphonyloxy or p-toluenesulphonyloxy). The alkylation is preferably effected in the presence of a suitable acid scavenger, for example, inorganic bases such as sodium or potassium carbonate, organic bases such as triethylamine, N,N-diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform at a temperature between ambient and the reflux tempelature of the solvent.

According to another example (b) of an alkylation process, a compound of general formula (I) in which $R^1$ represents a hydrogen atom may be prepared by alkylation of an amine of general formula (II) with a compound of general formula (IV):

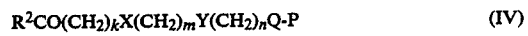
(IV)

in the presence of a reducing agent, followed where necessary by removal of any protecting groups.

Suitable reducing agents include hydrogen in the presence of a catalyst such as platinum, platinum oxide, palladium, palladium oxide, Raney nickel or rhodium, on a support such as charcoal, using an alcohol, e.g. ethanol or an ester e.g. ethyl acetate or an ether e.g. tetrahydrofuran, or water, as reaction solvent, or a mixture of solvents, e.g. a mixture of two or more of those just described at normal or elevated temperature and pressure, for example for 20° to 100° C. and from 1 to 10 atmospheres. Alternatively the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

Alkylation of an amine (II) with a compound of formula (IV) may result in formation of the intermediate imine of formula (V)

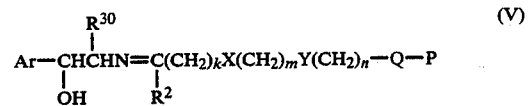
(V)

Reduction of the imine using the conditions described above, gives a compound of general formula (I).

In another general process (2), a compound of general formula (I) may be prepared by reduction. Thus, for example, a compound of general formula (I) may be prepared by reducing an intermediate of general formula (VI):

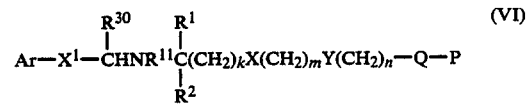
(VI)

(wherein $X^1$ represents a reducible group and $R^{11}$ represents a hydrogen atom or a protecting group) followed where necessary by removal of any protecting groups. Suitable reducible groups include those wherein $X^1$ is a group $>C=O$, and the reduction may for example be effected using reducing agents conveniently employed for the reduction of ketones. Thus when $X^1$ in general formula (VI) represents a $>C=O$ group this may be reduced to a —CH(OH)— group using, for example, a hydride such as diborane or a metal hydride such as lithium aluminium hydride, sodium bis(2-methoxyethoxy) aluminium hydride, sodium borohydride or aluminium hydride. The reaction may be effected in a solvent, where appropriate an alcohol e.g. methanol or ethanol, or an ether e.g. diethyl ether or tetrahydrofuran, or a halogenated hydrocarbon e.g. dichloromethane, at a temperature of 0° C. to the reflux temperature of the solvent. Alternatively, reduction may be effected using hydrogen in the presence of a catalyst as previously described for process (1) part (b).

In one convenient aspect of the reduction process, $R^{11}$ may be a protecting group which is capable of being removed under the reducing conditions used, for example hydrogen and a catalyst, thus avoiding the need for a separate deprotection step. Suitable protecting groups include arylmethyl groups such as benzyl, benzhydryl and α-methylbenzyl.

In the general processes described above, the compound of formula (I) obtained may be in the form of a salt, conveniently in the form of a physiologically acceptable salt. Where desired, such salts may be converted to the corresponding free bases using conventional methods. Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base. Alternatively, enantiomers of a compound of general formula (I) may be synthesized from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallization.

The intermediate compounds of general formula (VI) in which $X^1$ represents a group $>C=O$ may be prepared from a haloketone of formula (VII):

Ar—COCHHal     (VII)

(where Hal represents a halogen atom, and any hydroxyl and/or amino group(s) in the group Ar may optionally be protected) by reaction with an amine of general formula (VIII)

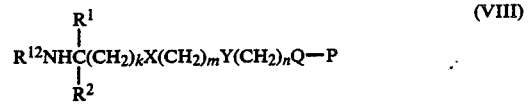

(wherein $R^{12}$ is a hydrogen atom or a group convertible thereto by catalytic hydrogenation).

The reaction may be effected in a cold or hot solvent, for example dimethylformamide, tetrahydrofuran, a halogenated hydrocarbon such as dichloromethane, or an ester such as ethyl acetate, in the presence of a base such as diisopropylethylamine.

The amines of formula (II) and haloketones of formula (VII) are either known compounds or may be prepared by methods analogous to those used for the preparation of the known compounds.

Intermediates of formula (III) may be prepared from the corresponding alcohols of formula (IX) using methods capable of effecting the conversion.

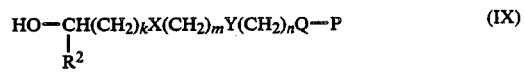

For example compounds of formula (III) where L represents a halogen atom may be prepared by reaction of the compounds of formula (IX) with a halogenating agent such as a triphenylphosphine-tetrahalogenomethane adduct (conveniently formed in situ e.g. by the reaction of triphenylphosphine and carbontetrabromide). The reaction may take place in the presence of a solvent such as a chlorinated hydrocarbon (e.g. dichloromethane) at a temperature range of 0°–30°.

Alcohols of formula (IX) may be prepared by reacting a compound of formula (X)

L-(CH$_2$)$_m$Y(CH$_2$)$_n$Q-P     (X)

(where L is as defined above) with a compound of formula (XI)

The reaction may take place optionally in a solvent such as an ether (e.g. tetrahydrofuran or 1,2-dimethoxyethane), an alcohol (e.g. methanol) or an amide (e.g. dimethylformamide) at a temperature up to the boiling point of the solvent. The reaction may be effected by first generating the anion of the compound of general formula (XI) by adding for example sodium, sodium hydride, potassium hydroxide or sodium hydroxide.

Compounds of formula (X) may be prepared from the corresponding compounds of formula (XII)

HO-(CH$_2$)$_m$Y(CH$_2$)$_n$Q-P     (XII)

using methods capable of effecting the conversion. For example when L in general formula (X) represents a hydrocarbylsulphonyloxy group (e.g. methanesulphonyloxy) such compounds may be prepared by reacting the compounds of formula (XII) with methanesulphonyl chloride in the presence of a base (e.g. triethylamine). The reaction conveniently takes place in the presence of a solvent such as a halogenated hydrocarbon (e.g. dichloromethane) at a temperature ranging from 0°-25°.

Compounds of formula (XII) may be prepared by reacting a compound of formula (XIII) with a compound of formula (XIV)

L-(CH$_2$)$_n$Q-P  (XIII)

HO(CH$_2$)$_m$YH  (XIV)

under conditions as described for the preparation of compounds of formula (IX) above.

Compounds of formula (XIII) are either known compounds or may be prepared from the corresponding alcohols as described for the preparation of compounds of formula (III) above.

Compounds of formulae (XI) and (XIV) are either known compounds or may be prepared by methods analogous to those used for the preparation of known compounds.

In addition, intermediates of formulae (III), (IV), (VIII), (X), (XII) and (XIII) may be prepared by methods analogous to those used for the preparation of known compounds. Suitable methods include those described in UK Patent Specifications Nos. 2140800A and 2159151A and in the exemplification included hereinafter.

The following examples illustrate the invention. Temperatures are in °C. 'Dried' refers to drying using magnesium sulphate or sodium sulphate. Unless otherwise stated, thin layer chromatography (t.l.c.) was carried out on silica, and flash column chromatography (FCC) was carried out on silica (Merck 9385), using one of the following solvent systems: A - ethyl acetate:cyclohexane; B - diethyl ether:cyclohexane; C - light petroleum (b.p. 40°-60°): diethyl ether; D - ethyl acetate:-methanol:triethylamine; E-toluene:ethanol: 0.88 ammonia; F- hexane: diethyl ether; G-toluene: ethanol: triethylamine; H- toluene: ethylacetate: triethylamine. The following abbreviations are used: DMF - dimethylformamide; THF - tetrahydrofuran; DMSO - dimethylsulphoxide; PE - light petroleum (b.p. 40°-60°); TAB - tetra-n-butylammonium hydrogen sulphate; DEA - N,N-diisopropylethylamine.

INTERMEDIATE 1 is α$^1$-(aminomethyl)-4-hydroxy-1,3-benzenedimethanol.

INTERMEDIATE 2

[4-[(6-Bromohexyl)oxy]butoxy]benzene

4-Phenoxy-1-butanol (4 g), 1,6-dibromohexane (6.7 ml), TAB (0.8 g) and sodium hydroxide (9.4 g in 18 ml water) were stirred at room temperature under nitrogen for 20 h. Water (80 ml) was added and the mixture extracted with diethyl ether (3×100 ml). The combined organic extracts were washed with water (50 ml), brine (50 ml), dried and evaporated to give a colourless liquid. This was applied to an FCC column and eluted with cyclohexane (2 l) and then with System A (1:40). The resulting oil was distilled to give the title compound (3.4 g) as a colourless oil b.p. 150°/3.5 mmHg T.l.c. (System A 1:6) Rf 0.3.

INTERMEDIATE 3

[[3-[(6-Bromohexyl)oxy]propyl]thio]benzene 3-(Phenylthio)-1-propanol (3.00 g), 1,6-dibromohexane (5.5 ml), aqueous 12.5M sodium hydroxide (27 ml) and TAB (802 mg) were vigorously stirred at room temperature overnight. The mixture was diluted with water (60 ml), extracted with diethyl ether (3×90 ml), and the combined, dried organic extracts were evaporated. The residual oil was purified by FCC eluting with System B (1:99→1:24) to give the title compound (4.01 g) as a colourless oil. T.l.c. (System B 1:3) Rf 0.35.

INTERMEDIATE 4

[2-[(6-Bromohexyl)oxy]ethoxy]benzene

2-Phenoxyethanol (2.76 g), 1,6-dibromohexane (14.6 g), TAB (1 g) and 50% sodium hydroxide (20 ml) were vigorously stirred for 21 h, added to water (100 ml) and extracted with diethyl ether (3×100 ml). The dried extract was evaporated and the residual colourless liquid (15 g) was purified by FCC eluting with cyclohexane followed by System A (1:1). Evaporation of the latter eluate gave the title compound (5.0 g) as a colourless liquid. T.l.c. (System A 1:1) Rf 0.6.

INTERMEDIATE 5

[[4-[(6-Bromohexyl)oxy]butyl]thio]benzene 4-(Phenylthio)-1-butanol (5.25 g), 1,6-dibromohexane (21.08 g), TAB (1 g) and 40% sodium hydroxide solution (45 ml) were stirred together at room temperature for 18 h. The mixture was diluted with water (150 ml), extracted with diethyl ether (2×150 ml), the organic layer washed with brine (100 ml), dried and evaporated in vacuo to give an oil. Purification by FCC eluting with System A (0:20→1:19) gave the title compound (5.54 g) as a colourless oil. T.l.c. (System A 1:9) Rf 0.12.

INTERMEDIATE 6

3-(4-Methoxyphenoxy)-1-propanol

To a solution of 4-methoxyphenol (1.24 g) and 3-bromopropanol (1.18 ml) in DMSO (15 ml) was added in one portion powdered sodium hydroxide (1.12 g). The mixture was stirred for 0.75 h then poured into 2N hydrochloric acid (100 ml) and extracted with ethyl acetate (100 ml). The organic phase was washed with water (100 ml), dried and concentrated to give the title compound (1.785 g) as a pale brown solid, m.p. 56°-60°.

INTERMEDIATE 7

1-[3-[(4-Bromobutyl)oxy]propoxy]-4-methoxybenzene

A mixture of Intermediate 6 (16.43 g), dibromobutane (42.9 ml), TAB (3.05 g), and 50% w/v sodium hydroxide solution (144 ml) was stirred at 20° for 20 h. Diethyl ether (400 ml) was added and the mixture washed with water (3×400 ml), dried and evaporated. The excess of dibromide was removed at 70° under high vacuum and the oily residue (~40 g) purified by FCC eluting with System C (8:1). The title compound (19.97 g) was obtained as a colourless oil. T.l.c. (System C 8:1) Rf 0.14.

INTERMEDIATE 8

6-[3-[4-(Methoxy)phenoxy]propoxy]-2-hexanone

A mixture of Intermediate 7 (1.268 g) and magnesium (100 mg) in dry diethyl ether (15 ml) containing a little iodine was heated under reflux for 2 h. This mixture was then cooled in an ice bath and treated with a solution of dimethylacetamide (0.37 ml) in diethyl ether (10 ml). After 1 h at 20° 3N hydrochloric acid (50 ml) was added and stirring continued at 20° for a further 0.5 h. The layers were separated and the organic phase was washed with 8% sodium bicarbonate solution (50 ml), dried and evaporated to give a white semi-solid. FCC eluting with System C (3:2 then 1:1) gave the title compound (284 mg) as a pale yellow oil. T.l.c. (System C 1:1) Rf 0.25.

INTERMEDIATE 9

3-(4-Bromophenoxy)-1-propanol

Powdered sodium hydroxide (2.2 g) was added to a solution of 4-bromophenol (3.46 g) and 3-bromopropanol (2.36 ml) in DMSO (18 ml). The mixture was stirred vigorously at 20° for 2.5 h then diluted with ethyl acetate (100 ml) and washed successively with 2N hydrochloric acid (100 ml), water (100 ml×2) and brine. Concentration of the dried organic phase yielded the title compound (5.02 g) as a pale orange oil. T.l.c. (diethyl ether) Rf 0.32.

INTERMEDIATE 10

1-Bromo-4-[3-[(6-bromohexyl)oxy]propoxy]benzene

A mixture of Intermediate 9 (4.48 g), 1,6-dibromohexane (11.9 ml), TAB (659 mg) and 50% aqueous sodium hydroxide solution (31 ml) was stirred vigorously at 21° for 19 h. Diethyl ether (200 ml) was added and the mixture washed with water (2×200 ml), dried and evaporated. The excess of dibromide was removed at 70°/1 mm Hg and the residue purified by FCC eluting with System C (8:1). The title compound (5.37 g) was obtained as a pale yellow oil. T.l.c. (System C 8:1) Rf 0.20.

INTERMEDIATE 11

4-[3-[(6-Bromohexyl)oxy]propoxy]benzoic acid

A solution of Intermediate 10 (1.97 g) in THF (20 ml) was cooled to −70° under nitrogen and treated with n-butyl lithium in hexane (1.6M; 3.44 ml). After 0.5 h powdered solid carbon dioxide (∼8 g) was added and the mixture allowed to warm to 20° over 1 h. THF was removed in vacuo and the residue diluted with water (150 ml), basified with 2N sodium hydroxide solution and washed with diethyl ether (100 ml). The aqueous phase was then acidified with 2N hydrochloric acid and extracted with diethyl ether (2×100 ml). Evaporation of these combined, dried extracts gave a white solid which was triturated with PE (2×10 ml) to yield the title compound (1.26 g) as a white powder, m.p. 72°–75°.

INTERMEDIATE 12

Propyl 4-[3-[(6-bromohexyl)oxy]propoxy]benzoate

A mixture of Intermediate 11 (1.0 g), ethereal hydrogen chloride (1 ml) and n-propanol (5 ml) was heated at ca 70° for 4 h. The pale brown solution was diluted with diethyl ether (50 ml), washed with 8% sodium bicarbonate solution (2×50 ml), dried and evaporated. The residual oil (1.05 g) was purified by FCC eluting with System C (2:1). The title compound (886 mg) was obtained as a colourless oil. T.l.c. (System C 1:1) Rf 0.46.

INTERMEDIATE 13

1-[[[3-[(6-Bromohexyl)oxy]]propyl]thio]-4-methylbenzene

3-[(4-Methylphenyl)thio]-1-propanol (4.0 g), 1,6-dibromohexane (16.06 g), 40% sodium hydroxide solution (40 ml) and TAB (1 g) were stirred together at room temperature for 18 h. The mixture was diluted with water (150 ml), extracted with ethyl acetate (2×150 ml), which was dried and evaporated in vacuo to give a colourless oil. Purification by FCC eluting with System A (0:20→1:19) gave the title compound (5.0 g) as a colourless oil. T.l.c. (System A 1:9) Rf 0.53.

INTERMEDIATE 14

2-[(6-Bromohexyl)oxy]ethoxy]-3,4-dimethylbenzene 2-(3,4-Dimethylphenoxy)ethanol (8.3 g), 1,6-dibromohexane (36.6 g), TAB (2 g) and 50% sodium hydroxide solution (50 ml) were vigorously stirred together for 17 h. The emulsion was added to water (150 ml) and extracted with diethyl ether (3×50 ml). The dried ethereal solution was evaporated to a colourless liquid (40.3 g) which was purified by FCC eluting with cyclohexane followed by System A (1:1) to yield the title compound (4.7 g) as a semi-solid, T.l.c. (System A 1:1) Rf 0.5.

INTERMEDIATE 15

[2-[(5-Bromopentyl)oxy]ethyl]thio]-4-chlorobenzene

2-[(4-Chlorophenyl)thio]ethanol (3.8 g), 1,5-dibromopentane (13.8 g), TAB (1 g) and 50% aqueous sodium hydroxide (20 ml) were stirred together for 17 h and extracted with diethyl ether (3×50 ml) and water (50 ml). The dried ethereal solution was evaporated and the residual colourless oil (15.0 g) was purified by FCC eluting with cyclohexane, followed by System A (1:1) to give the title compound (3.0 g), t.l.c. (System A 1:1) Rf 0.7.

INTERMEDIATE 16

3-(4-Bromophenoxy)-1-propanol

Powdered sodium hydroxide (2.2 g) was added to a solution of 4-bromophenol (3.46 g) and 3-bromopropanol (2.36 ml) in DMSO (18 ml). The mixture was stirred vigorously at 20° for 2.5 h then diluted with ethyl acetate (100 ml) and washed with 2N hydrochloric acid (100 ml), water (100 ml×2) and brine. Concentration of the dried organic phase yielded the title compound (5.02 g) as a pale orange oil. T.l.c. (diethyl ether) Rf 0.32.

INTERMEDIATE 17

1-Bromo-4-[3-[(6-bromohexyl)oxy]propoxy]benzene

A mixture of Intermediate 16 (4.48 g), 1,6-dibromohexane (11.94 ml), TAB (659 mg), and 50% aqueous sodium hydroxide solution (31 ml) was stirred vigorously at 21° for 19 h. Diethyl ether (200 ml) was added and the mixture washed with water (2×200 ml), dried and evaporated. The excess of dibromide was removed at 70°/1 mm Hg and the residue purified by FCC eluting with System C (8:1), to give the title compound (5.37 g) as a pale yellow oil. T.l.c. (System C 8:1) Rf 0.52.

INTERMEDIATE 18

4-[3-[(6-Bromohexyl)oxy]propoxy]benzoic acid

A solution of Intermediate 17 (1.97 g) in THF (20 ml) was cooled to −70° under nitrogen and treated with n-butyl lithium in hexane (1.6M; 3.44 ml). After 0.5 h powdered solid carbon dioxide (∼8 g) was added and the mixture allowed to warm to 20° over 1 h. THF was removed in vacuo and the residue diluted with water (150 ml), basified with 2N sodium hydroxide solution and washed with diethyl ether (100 ml). The aqueous phase was then acidified with 2N hydrochloric acid and extracted with diethyl ether (2×100 ml). Evaporation of the combined dried extracts gave a white solid which was triturated with PE to yield the title compound (1.26 g) as a white powder, m.p. 72°–75°.

INTERMEDIATE 19

4-[3-[(6-Bromohexyl)oxy]propoxy]benzoyl chloride

Intermediate 18 (5.0 g) in thionyl chloride (8 ml) was refluxed under nitrogen for 2 h. The solution was evaporated to give an oil and toluene was added. The solution was evaporated to give the title compound (5.37 g) as an orange oil. T.l.c. (System F 1:1) Rf 0.38.

INTERMEDIATE 20

[3-[(6-Bromohexyl)oxy]propoxy]-N,N-diethylbenzamide

Intermediate 19 (5.17 g) was added dropwise to diethylamine (1.1 g) in triethylamine (15 ml) with water-bath cooling. The reaction mixture was stirred at room temperature under nitrogen for 3 h and diluted with diethyl ether (50 ml). The solid was collected by filtration and the filtrate was concentrated to give an oil which was purified by FCC eluting with System F (4:3) to give the title compound (4.67 g) as a pale yellow oil. T.l.c. (System F 1:1)) Rf 0.13.

INTERMEDIATE 21

N,N-Diethyl-4-[3-[[6-[(phenylmethyl)amino]hexyl]oxy]propoxy]benzamide

Intermediate 20 (2.22 g) was added dropwise to benzylamine (8.0 ml) at 140° under nitrogen. The solution was stirred at 140° for 1 h, cooled, and partitioned between ethyl acetate (100 ml) and 8% aqueous sodium bicarbonate (70 ml). The dried organic layer was concentrated and benzylamine was distilled off (Kugelrohr) under vacuum. The residue was purified by FCC eluting with ethyl acetate- triethylamine (100:1) to give the title compound (1.80 g) as a pale yellow oil. T.l.c. (Ethyl acetate+few drops triethylamine) Rf 0.22.

INTERMEDIATE 22

4-[3-[[6-[[2-(4-Amino-3,5-dichlorophenyl)-2-hydroxyethyl](phenylmethyl)amino)hexyl]oxy]propoxy]-N,N-diethylbenzamide A solution of 1-(4-amino-3,5-dichlorophenyl)-2-bromoethanone (1.08 g), Intermediate 21 (1.68 g) and DEA (0.49 g) in THF (15 ml) was left to stand for 16 h at room temperature under nitrogen. The reaction mixture was filtered and the filtrate was concentrated to give an oil which in methanol (20 ml) was ice-cooled and treated portionwise with sodium borohydride (0.54 g). The reaction mixture was stirred at room temperature under nitrogen for 2 h and the solvent was evaporated. Water (70 ml) was added to the residue and extracted with ethyl acetate (3×50 ml). The combined extracts were washed with water (50 ml) and brine (50 ml), dried and concentrated to give an oil which was purified by FCC eluting with System G (97:3:1) to give the title compound (1.53 g) as a yellow oil. T.l.c. (System G 95:5:1)) Rf 0.25.

INTERMEDIATE 23

3-Phenoxy-1-propanol methanesulphonate

Methanesulphonyl chloride (16.15 g) was added dropwise to a stirred solution of 3-phenoxy-1-propanol (17.81 g) and triethylamine (23.78 g) in dry dichloromethane (120 ml) at 0° C. under nitrogen. The mixture was stirred at room temperature for 1 h and then washed successively with 2N hydrochloric acid (100 ml), water (100 ml), 8% sodium bicarbonate solution (100 ml) and brine (100 ml). The solution was dried and evaporated in vacuo to give an oil which solidified on standing to give the title compound (25.88 g) as a waxy solid. T.l.c. (diethyl ether) Rf 0.50.

INTERMEDIATE 24

2-(3-Phenoxypropoxy)ethanol

Sodium (2.80 g) was dissolved in 1,2-ethanediol (22.00 g) at ca 100° under nitrogen and 3-phenoxy-1-propanol methanesulphonate (25.5 g) in 1,2-dimethoxyethane (50 ml) was added dropwise at 100° under nitrogen. The mixture was stirred at 150° for 2 h and then carefully diluted with water (150 ml) and extracted with diethyl ether (2×150 ml). The combined organic extracts were washed with water (2×150 ml), dried and evaporated in vacuo to give the title compound (21.45 g) as an oil. T.l.c. System B (1:1) Rf 0.13.

In a similar manner to that described for Intermediate 23 and Intermediate 24 above, the following compounds were prepared:

INTERMEDIATE 25

2-(3-Phenoxypropoxy)ethanol methanesulphonate (3.23 g)

as an oil (purification by FCC eluting with System F(1:1)) was obtained from Intermediate 24 (5.0 g). T.l.c. (System F 1:1) Rf 0.10;

INTERMEDIATE 26

3-[2-(3-Phenoxypropoxy)ethoxy]-1-propanol (1.65 g)(purification by FCC eluting with diethyl ether) was obtained from Intermediate 25 (3.1 g) and 1,3-propanediol (2.84 g). T.l.c. (diethyl ether) Rf 0.22;

INTERMEDIATE 27

2-(3-Phenylpropoxy)ethanol methanesulphonate (23.19 g) as an oil was obtained from 2-(3-phenylpropoxy)ethanol (18.02 g). T.l.c. (diethyl ether) Rf 0.5

INTERMEDIATE 28

3-[2-(3-Phenylpropoxy)ethoxy]-1-propanol (9.30 g) (purification by FCC eluting with System B (2:3→1.1)) was obtained from Intermediate 27 (22.2 g) and 1,3-propanediol (21.68 g). T.l.c. (System B 1:1) Rf 0.2

INTERMEDIATE 29

2-(4-Phenylbutoxy)ethanol

Sodium (2.3 g) was dissolved in ethane-1,2-diol (18.6 g) under nitrogen benzenebutanol methanesulphonate (22.0 g) was added dropwise at ca 50°. The mixture was heated at 80°–100° for 2 h to give a heavy precipitate. THF (50 ml) was added and the resulting suspension was heated under reflux for 2 h and then treated with water (50 ml) before evaporating off the THF and extracting the residue with diethyl ether (2×100 ml). The dried extract was evaporated and the residue was distilled to give the title compound (12.5 g) as a colourless oil b.p. 110°–115°/0.2 mmHg (Kugelrohr).

INTERMEDIATE 30

2-(4-Phenylbutoxy)ethanol methanesulphonate

Methanesulphonyl chloride (7.5 g) was added dropwise to Intermediate 29 (12.0 g) and triethylamine (13.1 g) in dichloromethane (75 ml) at 0° under nitrogen. The resulting suspension was stirred at room temperature for 20 min and washed with hydrochloric acid (2M; 50 ml), water (25 ml), aqueous sodium bicarbonate (1M; 50 ml), and brine (50 ml). The dried organic phase was evaporated to give the title compound (15.7 g) as an oil. T.l.c. (diethyl ether) Rf 0.5

INTERMEDIATE 31

3-[2-(4-Phenylbutoxy)ethoxy]-1-propanol

Sodium (0.92 g) was dissolved in propane-1,3-diol (9.0 g) under nitrogen and Intermediate 30 (10.0 g) was added dropwise at ca 65°. The resulting mixture was heated at ca 100° for 2 h to produce a heavy precipitate. THF (50 ml) was added and the mixture was heated under reflux for 3 h, treated with water (50 ml) and THF was removed under reduced pressure. The residue was extracted with diethyl ether (2×100 ml) and the dried organic extract evaporated to give an oil, which was purified by FCC eluting with System B (2:3) to give the title compound (5.2 g) as a colourless oil. T.l.c. (diethyl ether) Rf 0.35.

INTERMEDIATE 32

[3-[2-(3-Bromopropoxy)ethoxy]propoxy]benzene

Triphenylphosphine (2.01 g) in dry dichloromethane (16 ml) was added dropwise over 20 min to a stirred solution of 3-[2-(3-phenoxypropoxy)ethoxy]-1-propanol (1.5 g), and carbon tetrabromide (2.54 g) in dry dichloromethane (27 ml) at 0° C. under nitrogen. The solution was allowed to warm to room temperature and stirred under nitrogen for 4 h. The solution was purified by FCC eluting with System F (4:1) to give the title compound (1.75 g) as a colourless oil. T.l.c. (System F 1:1) Rf 0.55

INTERMEDIATE 33

[3-[2-(3-Bromopropoxy)ethoxy]propyl]benzene

Triphenylphosphine (12.59 g), in dry dichloromethane was added dropwise over 20 min to a stirred solution of 3-[2-(3-phenylpropoxy)ethoxy]-1-propanol (8.8 g) and carbon tetrabromide (15.92 g) in dry dichloromethane (170 ml) at 0° C. under nitrogen. The solution was allowed to warm to room temperature and stirred under nitrogen for 30 min. The solution was concentrated to ca 30 ml and then purified by FCC eluting with System B (0:10→2:3) to give the title compound (9.94 g) as an oil. T.l.c. (System B 1:1) Rf 0.50

INTERMEDIATE 34

[4-[2-(3-Bromopropoxy)ethoxy]butyl]benzene

Triphenylphosphine (6.55 g) in dichloromethane (30 ml) was added dropwise to 3-[2-(4-phenylbutoxy)ethoxy]-1-propanol (5.0 g) and carbon tetrabromide (8.3 g) in dichloromethane (30 ml) at 0°. The mixture was stirred at room temperature for 1 h, evaporated onto silica, and purified by FCC eluting with cyclohexane - followed by System B (1:9) to give the title compound (5.4 g) as an oil. T.l.c. (System B 1:9) Rf 0.35

INTERMEDIATE 35

N-[3-[2-(3-Phenoxypropoxy)ethoxy]propyl]benzenemethanamine

[3-[2-(3-Bromopropoxy)ethoxy]propoxy]benzene (1.6 g) was added dropwise with stirring to benzylamine (2.70 g) at 130° under nitrogen. The solution was stirred at 130° under nitrogen for 2 h, cooled and diluted with ethyl acetate (150 ml), and washed with 2N hydrochloric acid (100 ml). The aqueous phase was re-extracted with ethyl acetate (2×100 ml) and the combined organic phases washed with 8% sodium bicarbonate solution (150 ml), dried and evaporated in vacuo to give the title compound (1.21 g) as an oil. T.l.c. (System E 40:10:1) Rf 0.52

INTERMEDIATE 36

N-[3-[2-(3-Phenylpropoxy)ethoxy]propyl]benzenemethanamine

[3-[2-(3-Bromopropoxy)ethoxy]propyl]benzene (3.01 g) was added dropwise over 5 min to benzylamine (5.35 g) at 120° under nitrogen. The solution was stirred at 130° for 4.5 h, cooled, diluted with ethyl acetate (200 ml) and washed with 2N hydrochloric acid (150 ml). The aqueous phase was re-extracted with ethyl acetate (2×100 ml) and the combined organic phases washed with 8% sodium bicarbonate solution (200 ml), dried and evaporated in vacuo to give the title compound (2.58 g) as an oil. T.l.c. (System E 40:10:1) Rf 0.49

INTERMEDIATE 37

Methyl [(3-pyridinyl)oxy]acetate

Sodium hydride (3.78 g, 80% suspension in oil) was added to a solution of 3-pyridinol (10 g) in THF (150 ml) at 0°. The mixture was stirred under nitrogen for 30 min, treated dropwise with methyl bromoacetate (19.3 g), heated under reflux for 24 h, poured into ice-water (200 ml) and extracted with ethyl acetate (2×100 ml). The combined organic extracts were dried and concentrated to give an oil which was purified by FCC, eluting with System G (98:2:1) to give the title compound (4 g), as an oil. T.l.c. (System E 80:20:1) Rf 0.46

INTERMEDIATE 38

2-[(3-pyridinyl)oxy]ethanol

Methyl [(3-pyridinyl)oxy]acetate (3.6 g) in diethyl ether (80 ml) was added dropwise to a stirred suspension of lithium aluminium hydride (826 mg) in diethyl ether (100 ml) at 0°. The mixture was stirred overnight at room temperature under nitrogen, water (1 ml) was added, followed by 2N sodium hydroxide (1 ml) and water (3 ml). The suspension was filtered and washed with ethyl acetate (3×100 ml) then dichloromethane (300 ml). The combined organic extracts were dried and concentrated to give the title compound (2.6 g) as an oil. T.l.c. (System E 80:20:1) Rf 0.31

INTERMEDIATE 39

3-[2-[(6-Bromohexyl)oxy]ethoxy]pyridine

A mixture of 2-[(3-pyridinyl)oxy]ethanol (1.9 g), 1,6-dibromohexane (6 ml), tetra-n-butylammonium bisulphate (0.5 g) and 50% w/v sodium hydroxide (20 ml) was stirred vigorously for 5 h, diluted with water (30 ml) and extracted with ethyl acetate (3×50 ml). The combined organic extracts were dried and evaporated in vacuo to give an oil which was purified by FCC eluting with hexane→ethylacetate to give the title compound (2.3 g) as an oil. T.l.c. (System E 80:20:1) Rf 0.63

INTERMEDIATE 40

N-[6-[2-[(3-Pyridinyl)oxy]ethoxy]hexyl]benzenemethanamine

A solution of 3-[[2-[(6-bromohexyl)oxy]ethyl]oxy]-pyridine (2 g) and benzylamine (10 ml) was stirred at 140° under nitrogen for 3 h. The solution was partitioned between 8% sodium bicarbonate (100 ml) and ethylacetate (100 ml). The organic extract was dried and distilled to give the title compound (1.8 g) as an oil. T.l.c. (System B 80:20:1) Rf 0.54

INTERMEDIATE 41

[4-Amino-3,5-dichloro-α-[[[3-[2-(3-phenoxypropoxy)ethoxy]propyl](phenylmethyl)amino]methyl]benzenemethanol 1-[4-Amino-3,5-dichlorophenyl]-2-bromoethanone (0.95 g), N-[3-[2-(3-phenoxypropoxy)ethoxy]propyl]-benzenemethanamine (1.15 g) and DEA (0.48 g) were stirred together in THF (35 ml) at room temperature under nitrogen for 7 h. The mixture was filtered and the filtrate evaporated in vacuo. The residue was dissolved in methanol (35 ml) and treated portionwise with sodium borohydride (0.34 g), at 0° C. under nitrogen, stirred at room temperature for 18 h, diluted with water (150 ml) and the solvent evaporated in vacuo. The residue was extracted with ethyl acetate (2×150 ml), dried and evaporated in vacuo to give an oil. Purification by FCC eluting with System H (95:5:1) gave the title compound (1.30 g) as an oil. T.l.c. (System H 90:10:1) Rf 0.39

INTERMEDIATE 42

4-Amino-3,5-dichloro-α-[[(phenylmethyl)[3-[2-(3-phenylpropoxy)ethoxy]propyl]amino]methyl]benzenemethanol 1-[4-Amino-3,5-dichlorophenyl]-2-bromoethanone (0.86 g), N-[3-[2-(3-phenylpropoxy)ethoxy]propyl]benzenemethanamine (1 g) and DEA (0.43 g) were stirred together in THF (30 ml) at room temperature under nitrogen for 22 h. The mixture was filtered and the filtrate evaporated in vacuo. The residue was dissolved in methanol (40 ml), treated portionwise with sodium borohydride (0.31 g) at 0° C. under nitrogen, stirred at room temperature under nitrogen for 2 h, diluted with water (150 ml) and extracted with ethyl acetate (2×150 ml). The dried extract was evaporated in vacuo to give an oil. Purification by FCC eluting with System F (1:1) gave the title compound (1.22 g) as an oil. T.l.c. (System F 1:1) Rf 0.19

INTERMEDIATE 43

4-Amino-3,5-dichloro-α-[[(phenylmethyl)[6-[2-[(3-pyridinyl)oxy]ethoxy]hexyl]amino]methyl]benzenemethane A solution of N-[6-[2-[(3-pyridinyl)oxy]ethoxy]hexyl]benzenemethanamine (18 g), 1-(4-amino-3,5-dichlorophenyl)-2-bromoethanone (1.7 g) and DEA (0.8 g) in THF (20 ml) was stirred under nitrogen overnight. The resulting precipitate was removed by filtration, the solvent evaporated and the residue dissolved in methanol (50 ml), and the solution cooled in an ice bath and treated portionwise with sodium borohydride (1.2 g). After 3 h, the solution was concentrated in vacuo to give an oil. The oil was partitioned between water (70 ml) and ethyl acetate (70 ml), the organic layer was washed with brine (70 ml), dried and concentrated to give an oil. Purification by FCC eluting with System G (95:5:1) gave the title compound (1.7 g) as an oil. T.l.c. (System E 80:20:1) Rf 0.61

INTERMEDIATE 44

2-[(2-Phenylethyl)thio]ethanol

Phenethylmercaptan (2.0 g) and potassium hydroxide (0.81 g) in methanol (15 ml) were stirred together under nitrogen for 15 min. 2-Chloroethanol (2.33 g) was added and the solution stirred under nitrogen for 6 h. 2N hydrochloric acid was added to acidify the mixture to pH5, and the methanol evaporated in vacuo. The residue was partitioned between water (100 ml) and diethyl ether (100 ml) and separated. The aqueous phase was re-extracted with diethyl ether (100 ml) and the combined ethereal layers dried and evaporated in vacuo to give an oil. Purification by FCC eluting with System F (3:1) gave the title compound (1.80 g) as a colourless oil. T.l.c. (diethyl ether) Rf 0.70

INTERMEDIATE 45

[2-[[2-[(4-Bromobutyl)oxy]ethyl]thio]ethyl]benzene

A mixture of 2-[(2-phenylethyl)thio]ethanol (1.0 g), 1,4-dibromobutane (3.79 g), TAB (0.6 g) and 50% aqueous sodium hydroxide (12 ml) was stirred at room temperature under nitrogen for 20 h. The mixture was diluted with water (100 ml), extracted with diethyl ether (2×100 ml), dried and evaporated in vacuo to give an oil. Purification by FCC eluting with cyclohexane followed by System B (5:95) gave the title compound (1.34 g) as a colourless oil. T.l.c. (System F 3:1) Rf 0.62.

INTERMEDIATE 46

2-[2-[2-(Phenylmethoxy)ethoxy]ethyl]pyridine

Sodium hydride (80% dispersion in oil, 1.68 g) was added portionwise to a solution of 2-pyridineethanol (6.88 g) in 1,2-dimethoxyethane (50 ml) and stirred under nitrogen for 18 h at room temperature. A solution of 2-(phenylmethoxy)ethanol methanesulphonate (8.25 g) in 1,2-dimethoxyethane (100 ml) was added and the mixture stirred at room temperature for 7 h, then poured into water (400 ml) and extracted with diethyl ether (3×200 ml). The ethereal extracts were washed with 2N hydrochloric acid (250 ml). The aqueous phase was re-extracted with diethyl ether (100 ml) and the aqueous phase carefully basified with 8% sodium bicarbonate to pH8. Extraction with diethyl ether (2×200 ml) and drying and evaporation in vacuo of the organic extracts gave an oil. Purification by FCC eluting with System F (4.1→1.1) gave the title compound (2.71 g) as an oil. T.l.c. (diethyl ether) Rf 0.54

INTERMEDIATE 47

2-[2-(2-Pyridinyl)ethoxy]ethanol hydrochloride

A solution of 2-[2-[2-(phenylmethoxy)ethyl]ethoxy]-pyridine (2.0 g) in absolute ethanol (60 ml) and ethanolic hydrochloric acid (1:9 HCl:EtOH 7.07 ml) was hydrogenated over pre-reduced 10% palladium oxide on charcoal catalyst (50% aqueous, 600 mg) until the uptake of hydrogen ceased (16 h). The mixture was filtered and evaporated in vacuo to give the title compound (1.66 g) as an oil which solidified on standing. T.l.c. (System G 95:5:1) Rf 0.08

INTERMEDIATE 48

2-[2-[2-[(6-Bromohexyl)oxy]ethoxy]ethyl]pyridine

A mixture of 2-[2-(2-pyridinyl)ethoxy]ethanol hydrochloride (1.55 g), 1,6-dibromohexane (5.94 g), TAB (0.5 g) and 50% sodium hydroxide (15 ml) was stirred at room temperature under nitrogen for 5 h. The mixture was diluted with water (100 ml), extracted with diethyl ether (2×150 ml) and evaporated in vacuo to give an oil. The residual oil was partitioned between 2N hydrochloric acid (100 ml) and hexane (2×100 ml). The aqueous phase was basified to pH12 with 50% sodium hydroxide, extracted with diethyl ether (2×150 ml), dried and evaporated in vacuo to give an oil. Purification by FCC eluting with System F (2:1→1:1) gave the title compound (1.62 g) as a colourless oil. T.l.c. (diethyl ether) Rf 0.40

INTERMEDIATE 49

N-[6-[2-[2-(2-Pyridinyl)ethoxy]ethoxy]hexyl]benzenemethanamine

A solution of 2-[2-[2-[(6-bromohexyl)oxy]ethoxy]ethyl]pyridine (1.55 g) in benzylamine (3.1 g) was heated at 125° under nitrogen for 3 h. The solution was allowed to cool and then partitioned between 8% sodium bicarbonate (100 ml) and diethyl ether (2×100 ml). The solvent was evaporated in vacuo and the residual oil distilled (Kugelrohr) to remove excess benzylamine. Purification by FCC eluting with System G 92:8:1) gave the title compound (1.38 g) as a colourless oil. T.l.c. (System G 95:5:1) Rf 0.14

INTERMEDIATE 50

4-Amino-3,5-dichloro-α-[[[6-[2-[2-(2-pyridinyl)ethoxy]ethoxy]hexyl](phenylmethyl)amino]methyl]benzenemethanol 1-[4-Amino-3,5-dichloro]-2-bromoethanone (0.99 g), N-[6-[2-[2-(2-pyridinyl)ethoxy)ethoxy]hexyl]benzenemethanamine (1.25 g) and DEA (0.50 g) were stirred together in THF (35 ml) at room temperature under nitrogen for 20 h. The mixture was filtered and the filtrate evaporated in vacuo. The residue was dissolved in methanol (20 ml) and sodium borohydride (0.36 g) was added portionwise to the solution at 0° C. under nitrogen. The mixture was stirred at room temperature for 1 h and then water (10 ml) was carefully added and the solvent evaporated in vacuo. The residue was partitioned between water (100 ml) and ethyl acetate (100 ml). The aqueous phase was re-extracted with ethyl acetate (100 ml) and the combined organic phases dried and evaporated in vacuo to give an oil. Purification by FCC eluting with System G (98:2:1) gave the title compound (1.19 g) as a colourless oil. T.l.c. (System G 95:5:1) Rf 0.24

INTERMEDIATE 51

2-[[2-(2-Pyridinyl)ethyl]thio]ethanol

2-Pyridineethanethiol (1.9 g) and potassium hydroxide (0.77 g) in methanol (15 ml) were stirred under nitrogen for 15 min. 2-Chloroethanol (1.10 g) was added and the solution stirred under nitrogen for 6 h. The mixture was acidified to pH5 with 2N hydrochloric acid and then left overnight. The methanol was evaporated in vacuo and the residue partitioned between water (150 ml) and diethyl ether (150 ml), separated and the aqueous phase re-extracted with diethyl ether (100 ml). The combined ethereal layers were dried and evaporated in vacuo to give an oil. Purification by FCC eluting with System G (98:2:1) gave the title compound (0.56 g) as a colourless oil. T.l.c. (diethyl ether) Rf 0.21

INTERMEDIATE 52

2-[2-[[2-[(6-Bromohexyl)oxy]ethyl]thio]ethyl]pyridine

A mixture of 2-[[2-(2-pyridinyl)ethyl]thio]ethanol (0.50 g), 1,6-dibromohexane (2.13 g), TAB (0.4 g) and 50% aqueous sodium hydroxide (6 ml) was stirred under nitrogen for 6 h, then diluted with water (75 ml) and extracted with diethyl ether (2×150 ml). The organic extracts were evaporated in vacuo to give an oil, which was partitioned between 2N hydrochloric acid (100 ml) and hexane (2×100 ml). The aqueous phase was basified to pH 12 with 50% aqueous sodium hydroxide and extracted with diethyl ether (2×150 ml), the dried organic extracts were evaporated in vacuo to give an oil. Purification by FCC eluting with System F (1:1) gave the title compound (0.60 g) as a colourless oil. T.l.c. (diethyl ether) Rf 0.64

EXAMPLE 1

4-Hydroxy-$\alpha^1$-[[[6-(4-(phenoxy)butoxy)hexyl]amino]methyl]-1,3-benzenedimethanol Intermediate 1 (2 g), [4-[(6-bromohexyl)oxy]butoxy]benzene (3 g) and DEA (2.3 ml) in DMF (30 ml) were stirred at 100° for 2 h. Saturated aqueous sodium bicarbonate (80 ml) was added and the mixture extracted with ethyl acetate (3×100 ml). The combined organic extracts were washed with water (50 ml), dried and evaporated. The resulting orange oil was applied to an FCC column and eluted with System D (89:10:1) to give an orange paste. Trituration with cyclohexane gave the title compound (1.7 g) as a brown solid m.p. 60°-68°. T.l.c. (System D 60:10:1) Rf 0.35.

EXAMPLE 2

4-Hydroxy-$\alpha^1$-[[[6-[3-(phenylthio)propoxy]hexyl]amino]methyl]-1,3-benzenedimethanol

[[3-[(6-Bromohexyl)oxy]propyl]thiobenzene (2.0 g), Intermediate 1 (1.51 g), DEA (1.71 ml) and DMF (22 ml) were stirred at 100° under nitrogen for 1 h. The cooled mixture was evaporated under reduced pressure and treated with aqueous saturated sodium bicarbonate (80 ml). The mixture was extracted with ethyl acetate (2×100 ml), and the combined extracts were washed with water (100 ml). The dried organic layer was evaporated and the residue in methanol (20 ml) was evaporated onto silica gel (Merck, 7734 10 g). The resultant silica gel plug was applied to an FCC column and elution with System D (89:10:1) afforded, after trituration with ethyl acetate, the title compound (617 mg) as a cream solid m.p. 89°-92°. T.l.c. (System D 90:10:1) Rf 0.14.

EXAMPLE 3

4-Hydroxy-$\alpha^1$-[[[6-[2-phenoxyethoxy)hexyl]amino]methyl]-1,3-benzenedimethanol Intermediate 1 (0.9 g), [2-[(6-bromohexyl)oxy]ethoxy]benzene (1.65 g) and DEA (1.2 ml) in DMF (20 ml) were stirred at 75° for 3 h. The solution was evaporated under reduced pressure and the resulting amber syrup (3.6 g) was partitioned between ethyl acetate and 8% sodium bicarbonate solution (100 ml). The organic extract was washed with water, the aqueous solutions were re-extracted with ethyl acetate (2×50 ml) and the combined organic extracts dried and evaporated. The residual yellow oil (2.04 g) was purified by FCC eluting with ethyl acetate and System D (85:15:1) to give a colourless oil (0.9 g). Further elution with the latter solvent mixture afforded the title compound (0.75 g) as a colourless oil, which when triturated with diethyl ether gave a white solid (0.45 g) m.p. 67°–68°.

Found: C,68.27; H,8.39; N,3.37.

$C_{23}H_{33}NO_5$ requires C,68.46; H,8.24; N,3.47%.

EXAMPLE 4

4-Hydroxy-$\alpha^1$-[[[6-[(4-phenylthio)butoxy]hexyl]amino]methyl]-1,3-benzenedimethanol benzoate A solution of [[4-[(6-bromohexyl)oxy]butyl]thio]benzene (1 g) in DMF (5 ml) was added dropwise to a stirred solution of Intermediate 1 (0.64 g) and DEA (1.24 g) in DMF (25 ml) at 70° under nitrogen. The solution was stirred at 70° under nitrogen for 2.5 h and evaporated in vacuo onto FCC silica. Purification by FCC eluting with System E (39:10:1) gave a colourless oil, which was dissolved in methanol (10 ml) and treated with benzoic acid (0.2 g). The solvent was evaporated and the residual oil triturated with diethyl ether to give the title compound (0.57 g) as a cream solid m.p. 108°–110°.

Found: C,67.4; H,7.7; N,2.5.

$C_{25}H_{37}NO_4S.C_7H_6O_2$ requires C,67.5; H,7.6; N,2.5%.

EXAMPLE 5

4-Hydroxy-$\alpha^1$-[[[5-[3-[(4-methoxy)phenoxy]propoxy]-1-methylpentyl]amino]methyl]-1,3-benzenedimethanol benzoate A solution of Intermediate 1 (0.33 g) and 6-[3-[4-(methoxy)phenoxy]propoxy]-2-hexanone (0.5 g) in absolute ethanol (25 ml) was hydrogenated over a mixture of pre-reduced 5% platinium oxide on charcoal (250 mg) and 10% palladium oxide on charcoal (250 mg) catalysts in absolute ethanol (10 ml). The mixture was filtered and evaporated in vacuo to give a product which was purified by FCC, elution with System E (39:10:1) affording an oil. This was dissolved in methanol (5 ml) and treated with benzoic acid (0.03 g), evaporated and triturated with diethyl ether to give the title compound (0.11 g) as a pale brown foam.

Found: C,65.05; H,7.63; N,2.37.

$C_{25}H_{37}NO_6.C_7H_6O_2.H_2O$ requires C,65.39; H,7.55; N,2.38%.

T.l.c. (System E 39:10:1) Rf 0.23.

EXAMPLE 6

Propyl 4-[3-[[6-[[2-hydroxy-2-[4-hydroxy-3-(hydroxymethyl)phenyl]ethyl]amino]hexyl]oxy]propoxy]benzoate Propyl 4-[3-[(6-bromohexyl)oxy]propoxy]benzoate (0.60 g) was added dropwise over 10 mins to a solution of Intermediate 1 (0.55 g) and DEA (0.56 g) in DMF (10 ml) stirred at 80° under nitrogen. The solution was stirred at 80° for a further 2 h, the solvent removed in vacuo at 60° and the residual oil partitioned between water (50 ml) and ethyl acetate (50 ml). The aqueous phase was extracted with further ethyl acetate (50 ml), the combined organic layers were dried and concentrated to yield a product which was purified by FCC, elution with System E (39:10:1) yielding the title compound (0.33 g) as a viscous colourless oil which solidified to a white powder on trituration with diethyl ether m.p. 75°–78°.

Found: C,66.74; H,8.30; N,2.66.

$C_{28}H_{41}NO_7$ requires C,66.78; H,8.21; N,2.78%.

EXAMPLE 7

4-Hydroxy-$\alpha^1$-[[[6-[3-[(4-methylphenyl)thio]propoxy]hexyl]amino]methyl]-1,3-benzenedimethanol hydrobromide A solution of 1-[[[3-[(6-bromohexyl)oxy]propyl]thio]-4-methylbenzene (1 g) in DMF (5 ml) was added dropwise to a stirred solution of Intermediate 1 (0.64 g) and DEA (1.24 g) in DMF (25 ml) at 70° under nitrogen. The solution was stirred at 70° under nitrogen for 2 h and evaporated in vacuo onto FCC silica. Purification by FCC on triethylamine deactivated silica (Merck 9385) eluting with toluene-ethanol (8:1) gave a colourless oil, which on trituration with diethyl ether gave the title compound (0.3 g) as a white solid m.p. 74°–76°.

Found: C,57.3; H,7.4; N,2.7.

$C_{25}H_{37}NO_4S.HBr$ requires C,56.8; H,7.25; N,2.65%.

EXAMPLE 8

$\alpha^1$-[[[6-[2-(3,4-Dimethylphenoxy)ethoxy]hexyl]amino]methyl]-4-hydroxy-1,3-benzenedimethanol A solution of [2-[(6-bromohexyl)oxy]ethoxy]-3,4-dimethylbenzene (1.82 g), Intermediate 1 (0.9 g) and DEA (1.2 ml) in DMF (20 ml) was stirred at 70° for 3 h, evaporated under reduced pressure and the residual brown gum was extracted into 8% sodium bicarbonate solution (50 ml) and ethyl acetate (3×50 ml). The dried ethyl acetate solution was evaporated under reduced pressure and the residual oil (1.9 g) was purified by FCC. Elution with ethyl acetate followed by System D (85:15:1) gave an amber oil (0.55 g) which was triturated with diethyl ether (2×30 ml). Evaporation of the ethereal solution gave the title compound (0.14 g) as a white solid m.p. 65°–68°.

Assay Found: C,69.39; H,8.79; N,3.12.

$C_{25}H_{37}NO_5$ requires C,69.58; H,8.64; N,3.25%.

EXAMPLE 9

$\alpha^1$-[[[5-[2-(4-Chlorophenylthio)ethoxy]pentyl]amino]methyl]-4-hydroxy-1,3-benzenedimethanol A solution of [[2-[(5-bromopentyl)oxy]ethyl]thio]-4-chlorobenzene (1.85 g), Intermediate 1 and DEA (1.2 ml) in DMF (20 ml) was stirred for 70° for 3 h, evaporated under reduced pressure and the residual amber oil treated with 8% sodium bicarbonate solution (50 ml) and water (50 ml). The mixture was extracted with ethyl acetate (3×100 ml) which was dried and evaporated. The resulting liquid (2.25 g) was purified by FCC eluting with ethyl acetate followed by System D (85:15:1) to give an oil (0.6 g) which when treated with diethyl ether gave the title compound (0.5 g) as a white solid m.p. 69°–73°

Assay Found: C,60.06; H,6.93; N,3.05.

$C_{22}H_{30}ClNO_4S$ requires C,60.05; H,6.87; N,3.18%.

EXAMPLE 10

4-[3-[[6-[[2-(4-Amino-3,5-dichlorophenyl)-2-hydroxyethyl]amino]hexyl]oxy]propoxy]-N,N-diethylbenzamide (E)-butenedioate 4-[3-[[6-[[2-(4-Amino-3,5-dichlorophenyl)-2-hydroxyethyl](phenylmethyl)amino]hexyl]oxy]propoxy]-N,N-diethylbenzamide (1.45 g) was hydrogenated over pre-reduced 10% palladium on carbon (50% aqueous paste, 310 mg) in ethanol (15 ml) containing hydrochloric acid (conc. HCl/EtOH, 1:9 v/v, 2.1 ml). The catalyst was removed by filtration the solvent was evaporated and the residue was partitioned between 8% sodium bicarbonate (20 ml) and ethyl acetate (20 ml). The aqueous layer was re-extracted with ethyl acetate (20 ml) and the combined organic extracts were washed with 8% sodium bicarbonate and brine, dried and concentrated to a slightly coloured oil which was purified by FCC eluting with System G (90:10:1) to give a colourless oil (840 mg). A solution of the oil (810 mg) and fumaric acid (180 mg) in methanol (10 ml) was concentrated to an oil which was triturated several times with diethyl ether to give the title compound (670 mg) as an off white powder. T.l.c. (System E 80:20:2) Rf 0.56.

Analysis Found: C,58.66; H,6.99; N,6.60; Cl,11.96.

$C_{28}H_{41}Cl_2N_3O_4.0.5C_4H_4O_4$ requires C,58.82; H,7.08; N,6.86; Cl,11.57%.

EXAMPLE 11

N,N-Diethyl-4-[3-[[6-[[2-[4-hydroxy-3-[(methylsulphonyl)amino]phenyl]ethyl]amino]hexyl]oxy]-propoxy]benzamide benzoate A solution of N-[5-(bromoacetyl)-2-(phenylmethoxy)phenyl]-methanesulphonamide (1.5 g), N,N-diethyl-4-[3-[[6-[(phenylmethyl)amino]hexyl]oxy]propoxy]benzamide (1.56 g) and DEA (0.54 g) in dichloromethane (35 ml) was stirred at room temperature under nitrogen for 4 h. The solvent was evaporated and the residual oil in ethanol (130 ml) was hydrogenated over pre-reduced 10% palladium on charcoal (50% paste in water, 0.7 g) and 5% platinum on charcoal (0.8 g). The reaction mixture was filtered and the solvent was evaporated. The residual oil was purified by FCC eluting with System E (80:20:2) to give a foam (544 mg) which was dissolved in methanol (5 ml) and treated with benzoic acid (124 mg) in methanol (5 ml). The solution was concentrated and the residue was triturated with diethyl ether for five days to give the title compound (510 mg) as a white solid, m.p. 75°-77°.

Analysis Found: C,60.8; H,7.5; N,5.9; S,4.6.

$C_{29}H_{45}N_3O_7S.C_7H_6O_2.0.5H_2O$ requires C,60.8; H,7.4; N,5.9;

EXAMPLE 12

4-Hydroxy-$\alpha^1$-[[[3-[2-(4-phenylbutoxy)ethoxy]propyl]amino]methyl]-1,3-benzenedimethanol benzoate

[4-[2-(3-Bromopropoxy)ethoxy]butyl]benzene (2.0 g) was added dropwise to Intermediate 1 (1.3 g) and DEA (1.7 g) in DMF (20 ml) at 70°. The solution was heated at 70°-75° for 2 h and evaporated, and the residue was purified by FCC eluting with System E (80:20:1) to give a yellow gum. The gum (0.8 g) in chloroform was treated with benzoic acid (0.6 g) and evaporated. The residue was triturated with diethyl ether (2×50 ml) to give the title compound (0.9 g) as a yellow gum. T.l.c. (System E 80:20:1) Rf 0.5

Analysis Found: C,68.7; H,7.8; N,2.4.

$C_{24}H_{35}NO_5.C_7H_6O_2$ requires C,69.0; H,7.7; N,2.6%.

EXAMPLE 13

4-Amino-3,5-dichloro-α-[[[3-[2-(3-phenoxypropoxy)ethoxy]propyl]amino]methyl]benzenemethanol (E)-2-butenedioate

[4-Amino-3,5-dichloro-α-[[[3-[2-(3-phenoxypropoxy)ethoxy]propyl](phenylmethyl)amino]methyl]benzenemethanol (1.2 g) was hydrogenated over pre-reduced 10% palladium oxide on charcoal catalyst (50% aqueous, 220 mg) in ethanol (15 ml) containing hydrochloric acid (1:9 conc. hydrochloric acid/ethanol, 1.99 ml) until the uptake of hydrogen (54 ml) ceased. The mixture was filtered and evaporated in vacuo. The resulting brown oil was dissolved in ethyl acetate (100 ml) and basified with 8% sodium bicarbonate solution (150 ml). The aqueous phase was re-extracted with ethyl acetate (50 ml) and the combined organic phases were dried and evaporated in vacuo to give an oil. Purification by FCC eluting with System H (90:10:1→90:20:1) gave a colourless oil (0.55 g). This was dissolved in methanol (15 ml), treated with fumaric acid (0.07 g), evaporated in vacuo and triturated with diethyl ether to give the title compound (0.52 g) as a white solid; m.p. 97°-98.5°. T.l.c. (System E 40:10:1) Rf 0.21

EXAMPLE 14

4-Amino-3,5-dichloro-α-[[[3-[2-(3-phenylpropoxy)ethoxy]propyl]amino]methyl]benzenemethanol (E)-butendioate A solution of [4-amino-3,5-dichloro-α-[[(phenylmethyl)[3-[2-(3-phenylpropoxy)ethoxy]propyl]amino]methyl]benzenemethanol (1.10 g) and 1:9 conc. hydrochloric acid in ethanol (1.88 ml) in absolute ethanol (16 ml) was hydrogenated over pre-reduced 10% palladium oxide on charcoal (50% aqueous paste 210 mg) in absolute ethanol (5 ml) until the uptake of hydrogen (56.9 ml) ceased. The mixture was filtered and evaporated in vacuo to give a brown oil (1.09 g). Trituration with diethyl ether gave a solid, which was dissolved in ethyl acetate (150 ml) and basified with 8% sodium bicarbonate solution (100 ml). The aqueous phase was re-extracted with ethyl acetate (50 ml) and the combined organic phases dried and evaporated in vacuo. The resulting brown oil, (0.27 g) was dissolved in methanol (10 ml) and treated with fumaric acid (0.04 g). The solution was evaporated in vacuo and the residue triturated with diethyl ether to give the title compound (0.32 g) as a white solid m.p. 89.5°-91°.

T.l.c. (System E 40:10:1) Rf 0.42.

EXAMPLE 15

4-Amino-3,5-dichloro-α-[[[6-[2-[(3-pyridinyl)oxy]ethoxy]hexyl]amino]methyl]benzenemethanol (E)-butenedioate 4-Amino-3,5-dichloro-α-[[(phenylmethyl)[6-[2-[(3-pyridinyl)oxy]ethoxy]hexyl]amino]methyl]benzenemethanol (1 g;) was hydrogenated over pre-reduced palladium oxide on carbon (50% aqueous paste, 200 mg) in ethanol (30 ml) containing conc. hydrochloric acid for 6 h (uptake of hydrogen, 45 ml). The catalyst was removed by filtration the solvent was evaporated and the residual oil was partitioned between 8% sodium bicarbonate (50 ml) and ethyl acetate (50 ml). The organic layer was dried and concentrated to give a yellow oil which was purified by FCC eluting with System G (95:5:1) to give an oil (590 mg). The oil was dissolved in methanol (20 ml) and treated with fumaric acid (77 mg) and concentrated to give a foam which was triturated in ethyl acetate to give the title compound (650 mg) as a white solid—m.p. 105°-106°.

T.l.c. (System E 80:20:1) Rf 0.43.

EXAMPLE 16

[4-Amino-3,5-dichloro-α-[[[4-[2-[(2-phenylethyl)thio]ethoxy]butyl]amino]methyl]benzenemethanol A solution of 4-amino-α-(aminomethyl)-3,5-dichlorobenzenemethanol (1.53 g), [2-[[2-(4-bromobutoxy)ethyl]thio]ethyl]benzene (1.0 g) and DEA (0.71 g) in DMF (20 ml) was stirred under nitrogen at 100° for 2 h. The solvent was evaporated in vacuo and the residue purified by FCC eluting with System G (95:5:1) to give an oil. The oil was partitioned between dichloromethane (50 ml) and 8% sodium bicarbonate (75 ml) and the aqueous solution re-extracted with dichloromethane (50 ml). The organic extracts were dried and evaporated in vacuo to give the title compound (924 mg,) as a white solid m.p. 74°–77°.

T.l.c. (System E 40:10:1) Rf 0.57

EXAMPLE 17

4-Amino-3,5-dichloro-α-[[[6-[2-[2-(2-pyridinyl)ethoxy]ethoxy]hexyl]amino]methyl]benzenemethanol A solution of 4-amino-3,5-dichloro-α-[[(phenylmethyl)[6-[2-[2(2-pyridinyl)ethoxy]ethoxy]hexyl]amino]methyl]benzenemethanol (1.1 g,) in ethanol (25 ml) was hydrogenated over pre-reduced 10% palladium oxide on charcoal catalyst (50% aqueous paste, 600 mg) in ethanol (10 ml) containing 1:9 conc. hydrochloric acid/ethanol, (1.78 ml,) until the uptake of hydrogen ceased (1 h). The mixture was filtered and evaporated in vacuo to give an oil which was dissolved in dichloromethane (100 ml) and washed with 8% sodium bicarbonate (50 ml). The aqueous phase was re-extracted with dichloromethane (50 ml) and the combined organic phases dried and evaporated in vacuo to give an oil. Purification by FCC eluting with System G (95:5:1) gave a colourless oil, which was dissolved in methanol (10 ml) and treated with fumaric acid (0.09 g), evaporated in vacuo and triturated with diethyl ether to give a white solid (0.75 g,). The solid was dissolved in dichloromethane (150 ml) and washed with 8% sodium bicarbonate (100 ml). The aqueous layer was re-extracted with dichloromethane (100 ml) and the combined organic fractions dried and evaporated in vacuo to give an oil. Trituration with System F (ca. 10:1) gave the title compound (0.60 g,) as a white solid m.p. 45.5°–46.5°. T.l.c. (System E 40:10:1) Rf 0.49.

EXAMPLE 18

[4-Amino-3,5-dichloro-α-[[[6-[2-[[2-(2-pyridinyl)ethyl]thio]ethoxy]hexyl]amino]methyl]benzenemethanol A solution of 4-amino-α-(aminomethyl)-3,5-dichlorobenzenemethanol (0.56 g,), 2-[2-[[2-[(6-bromohexyl)oxy]ethyl]thio]ethyl]pyridine (0.58 g,) and DEA (0.26 g,) in DMF (10 ml) was stirred under nitrogen for 2 h. The solvent was evaporated in vacuo and the residual oil partitioned between 8% sodium bicarbonate solution (100 ml) and dichloromethane (100 ml). The aqueous phase was re-extracted with dichloromethane (100 ml) and the combined organic phases dried and evaporated in vacuo to give an oil. Purification by FCC eluting with System G (98:2:1) gave an oil. Trituration with hexane afforded the title compound (451 mg,) as a solid m.p. 59.5°–62°. T.l.c. (System E 40:10:1) Rf 0.32.

The following are examples of suitable formulations of compounds of the invention. The term 'active ingredient' is used herein to represent a compound of the invention.

TABLETS (DIRECT COMPRESSION)

|  | mg/tablet |
|---|---|
| Active ingredient | 2.0 |
| Microcrystalline cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

The tablets may be film coated with suitable film forming materials, such as hydroxypropylmethylcellulose, using standard techniques. Alternatively, the tablets may be sugar coated.

METERED DOSE PRESSURISED AEROSOL (SUSPENSION AEROSOL)

|  | mg/metered dose | Per can |
|---|---|---|
| Active ingredient micronised | 0.100 | 26.40 mg |
| Oleic Acid BP | 0.010 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic acid is mixed with the trichlorofluoromethane at a temperature of 10°–15° C. and the micronised drug is mixed into the solution with a high shear mixer. The suspension is metered into aluminium aerosol cans and suitable metering valves delivering 85 mg of suspension are crimped onto the cans and the dichlorodifluoromethane is pressure filled into the cans through the valves.

INHALATION CARTRIDGES

|  | mg/cartridge |
|---|---|
| Active ingredient micronised | 0.200 |
| Lactose BP to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents in the cartridges are administered using a powder inhaler such as the Glaxo Rotahaler.

We claim:

1. A compound of formula (I)

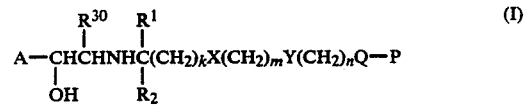

or a physiologically acceptable salt or solvate thereof wherein

Ar represents a group

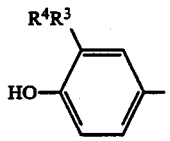

where
R³ is a C$_{1-2}$alkylene group,
R⁴ is a hydroxy group;
k represents an integer from 1 to 8;
m represents zero or an integer from 2 to 7 and
n represents an integer from 2 to 7, wherein the sum total of
k, m and n is 4 to 12;
R¹ and R² each represents a hydrogen atom or a methyl or ethyl group, wherein the sum total of carbon atoms in R¹ and R² is not more than 2;
R³⁰ represents hydrogen or C$_{1-2}$alkyl;
X and Y each represent an oxygen atom;
Q represents a bond;
P represents a phenyl group, or a phenyl group substituted by one or more substituents selected from halogen atoms, or the groups C$_{1-3}$alkyl, C$_{1-3}$alkoxy, hydroxy, —CH$_2$OH and —(CH$_2$)$_2$OH.

2. A compound according to claim 1 wherein the chain —(CH$_2$)$_k$— is a group selected from —CH$_2$—, —(CH$_2$)$_2$—, —(CH$_2$)$_3$—, —(CH$_2$)$_4$—, —(CH$_2$)$_5$—, —(CH$_2$)$_6$— and —(CH$_2$)$_7$— and the chains —(CH$_2$)$_m$— and —(CH$_2$)$_n$— are each groups selected from —(CH$_2$)$_2$—, —(CH$_2$)$_3$—, —(CH$_2$)$_4$—, —(CH$_2$)$_5$ and —(CH$_2$)$_6$—, or the chain —(CH$_2$)$_m$— is a bond, subject to the proviso that the sum total of k, n and m is 4 to 12.

3. A compound according to claim 1 wherein the sum total of carbon atoms in the chains —(CH$_2$)$_k$—, —(CH$_2$)$_m$— and —(CH$_2$)$_n$— is 7, 8 or 9.

4. A compound according to claim 1 wherein R¹ and R² are each a hydrogen atom or a methyl group.

5. A compound according to claim 1 wherein R³⁰ is a hydrogen atom.

6. A compound according to claim 1 wherein Ar is a group of type (b), (c) or (d) as defined in claim 1 or a group of formula

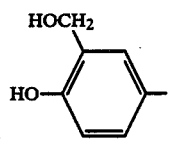 (f)

or

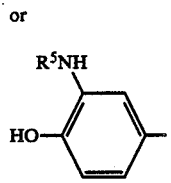 (i)

where R⁵ is HCO—, NH$_2$CO— or CH$_3$SO$_2$—.

7. A compound according to claim 1 wherein P is a phenyl group or a phenyl group containing one or two substituents selected from halogen atom(s), C$_{1-3}$alkyl and C$_{1-3}$alkoxy groups.

8. The compound 4-hydroxy-α¹-[[[3-[2-(4-phenylbutoxy)ethoxy)propyl]amino]methyl]-1,3-benzenedimethanol.

9. A pharmaceutical composition for therapy or prophylaxis of a disease associated with reversible airways obstruction such as asthma or chronic bronchitis, which comprises an effective amount to alleviate said disease of at least one compound of formula (I) as defined in claim 1 or a physiologically acceptable salt or solvate thereof, together with a physiologically acceptable carrier or excipient.

10. A method of therapy or prophylaxis of a disease associated with reversible airways obstruction such as asthma or chronic bronchitis in a patient which comprises administering to said patient an effective amount to alleviate said disease of a compound of formula (I) as defined in claim 1 or a physiologically acceptable salt or solvate thereof.

* * * * *

UNITED STATES PATENT AND TRADEMARK OFFICE
CERTIFICATE OF CORRECTION

PATENT NO. : 4,937,268
DATED : June 26, 1990
INVENTOR(S) : Ian F. Skidmore, et al.

It is certified that error appears in the above-identified patent and that said Letters Patent is hereby corrected as shown below:

Column 28, line 64, change "A" to --Ar--.

Column 30, delete claim 6 completely.

Signed and Sealed this

Fourteenth Day of September, 1993

Attest:

BRUCE LEHMAN

*Attesting Officer*  *Commissioner of Patents and Trademarks*